(12) United States Patent
Wang et al.

(10) Patent No.: US 11,426,541 B2
(45) Date of Patent: Aug. 30, 2022

(54) MEDICATION DISPENSER

(71) Applicant: Jabil Circuit (Shanghai) Co., Ltd., Shanghai (CN)

(72) Inventors: Zhe-Heng Wang, Shanghai (CN); Ying Li, Shanghai (CN)

(73) Assignee: Jabil Circuit (Shanghai) Co., Ltd., Shanghai (CN)

( * ) Notice: Subject to any disclaimer, the term of this patent is extended or adjusted under 35 U.S.C. 154(b) by 436 days.

(21) Appl. No.: 16/564,677

(22) Filed: Sep. 9, 2019

(65) Prior Publication Data

US 2020/0078538 A1 Mar. 12, 2020

(30) Foreign Application Priority Data

Sep. 11, 2018 (CN) .......................... 201811056217.9

(51) Int. Cl.
*A61M 15/00* (2006.01)
(52) U.S. Cl.
CPC ...... *A61M 15/008* (2014.02); *A61M 15/0021* (2014.02); *A61M 15/0065* (2013.01); *A61M 2205/3317* (2013.01)
(58) Field of Classification Search
CPC ............ A61M 15/001; A61M 15/0021; A61M 15/0086; A61M 15/0091; A61M 2202/0078; A61M 2202/064; A61M 2205/502; A61M 2205/8206; A61M 16/109; A61M 16/1095; A61M 16/1085; A61M 16/0875; A61M 16/0816; A61M 16/16; A61M 16/0066; A61M 2016/0039; A61M 15/06; A61M 15/0043; A61M 16/161; A61M 2016/0024; A61M 2016/0027; A61M 2016/1025; A61M 2016/1035; A61M 2205/3368; A61M 2205/3633; A61M 2205/3653; A61M 2205/50; A61M 2205/583; A61M 2240/00; A61M 15/0085; A61M 15/009; A61M 15/0051; A61M 15/004; A61M 15/008; A61M 11/002; A61M 15/0008; A61M 15/0036; A61M 15/0055; A61M 2205/332; A61M 2205/3569; A61M 2205/3592; A61M 2205/52; A61M 2205/8212; A24F 40/00; A24F 40/05; A24F 40/20;

(Continued)

(56) References Cited

U.S. PATENT DOCUMENTS

| 2005/0154491 A1* | 7/2005 | Anderson | A61M 15/00 700/236 |
| 2015/0025499 A1* | 1/2015 | Trock | A61M 5/14236 604/506 |
| 2018/0093052 A1* | 4/2018 | Li | A61M 15/008 |

FOREIGN PATENT DOCUMENTS

CN 107890598 A 4/2018

* cited by examiner

*Primary Examiner* — Elliot S Ruddie
(74) *Attorney, Agent, or Firm* — Young Basile Hanlon & MacFarlane, P.C.

(57) ABSTRACT

A medication dispenser includes a casing, a notched wheel and a circuitry unit. The casing includes a mouthpiece. The notched wheel has a plurality of notches, and is rotatable to register the notches with the mouthpiece. The circuitry unit includes an annular magnetic member co-rotatably mounted to the notched wheel, and a Hall sensor. The magnetic member has a plurality of alternately arranged first and second magnetic poles. The Hall sensor is in a first detecting state when it detects one of the first magnetic poles, and is in a second detecting state when it detects one of the second magnetic poles.

20 Claims, 5 Drawing Sheets

(58) Field of Classification Search
CPC ......... A24F 40/40–42; A24F 40/50–65; H05B 1/025; H05B 3/56; H05B 2203/022; A61G 11/00; F16L 11/118; F16L 53/38
See application file for complete search history.

MEDICATION DISPENSER

CROSS-REFERENCE TO RELATED APPLICATION

This application claims priority of Chinese Invention Patent Application No. 201811056217.9, filed on Sep. 11, 2018.

FIELD

The disclosure relates to a medication dispenser, and more particularly to a medical inhaler.

BACKGROUND

A conventional medical inhaler disclosed in Chinese Application Publication No. 107890598 includes a rotatable notched wheel and a circuitry unit. The circuitry unit includes a plurality of magnets that are mounted to the notched wheel, and a Hall sensor that is disposed adjacent to the notched wheel. The Hall sensor detects movement of the magnetic field of the magnets so as to detect rotational angle of the notched wheel. However, it is laborious to mount the magnets on the notched wheel with the polarity of the magnets being accurately arranged.

SUMMARY

Therefore, an object of the disclosure is to provide a medication dispenser that can alleviate the drawback of the prior art.

According to one aspect of the disclosure, the medication dispenser includes a casing, a dispenser unit and a circuitry unit. The casing includes a mouthpiece. The dispenser unit is disposed in the casing and includes at least one dispenser assembly. The at least one dispenser assembly includes a notched wheel. The notched wheel has an end surface, and a plurality of notches that are formed in an outer surrounding surface thereof for retaining a plurality of doses of medication. The notched wheel is rotatable relative to the casing so as to register the notches with the mouthpiece. The circuitry unit is disposed in the casing, and includes a circuit board, an annular magnetic member that is co-rotatably mounted to the end surface of the notched wheel, and a Hall sensor that is disposed adjacent to the magnetic member. The magnetic member has a plurality of first and second magnetic poles that are alternately arranged. The Hall sensor is in a first detecting state when it detects one of the first magnetic poles, and is in a second detecting state when it detects one of the second magnetic poles.

According to another aspect of the disclosure, the medication dispenser includes a casing, at least one notched wheel and a circuitry unit. The casing includes a mouthpiece. The notched wheel is disposed in the casing, and has a plurality of equidistantly and angularly spaced-apart notches that are formed in an outer surrounding surface thereof for retaining a plurality of doses of medication. The notched wheel is rotatable relative to the casing so as to register the notches with the mouthpiece. The circuitry unit is disposed in the casing, and includes a circuit board, an annular magnetic member that is co-rotatably mounted to the end surface of the notched wheel, and a Hall sensor that is disposed adjacent to the magnetic member. The magnetic member has a plurality of first and second magnetic poles that are alternately arranged. The Hall sensor is in a first detecting state when it detects one of the first magnetic poles, and is in a second detecting state when it detects one of the second magnetic poles. It is determined that one of the first and second magnetic poles is detected by the Hall sensor when the strength of the magnetic field generated by the one of the first and second magnetic poles exceeds a predetermined threshold.

According to another aspect of the disclosure, the medication dispenser includes a casing, at least one notched wheel and a circuitry unit. The notched wheel is disposed in the casing, and has a plurality of equidistantly and angularly spaced-apart notches that are formed in an outer surrounding surface thereof for retaining a plurality of doses of medication. The notched wheel is rotatable relative to the casing so as to permit the doses in the notches to be inhaled. The circuitry unit is disposed in the casing, and includes a magnetic member that is co-rotatably mounted to the notched wheel, and a Hall sensor that is for detecting the magnetic member. The magnetic member has a plurality of first and second magnetic poles that are alternately arranged in a circumferential direction thereof. Upon rotation of the magnetic member along with the notched wheel, the Hall sensor switches between a first detecting state in which one of the first magnetic poles is detected by the Hall sensor, and a second detecting state in which one of the second magnetic poles is detected by the Hall sensor.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
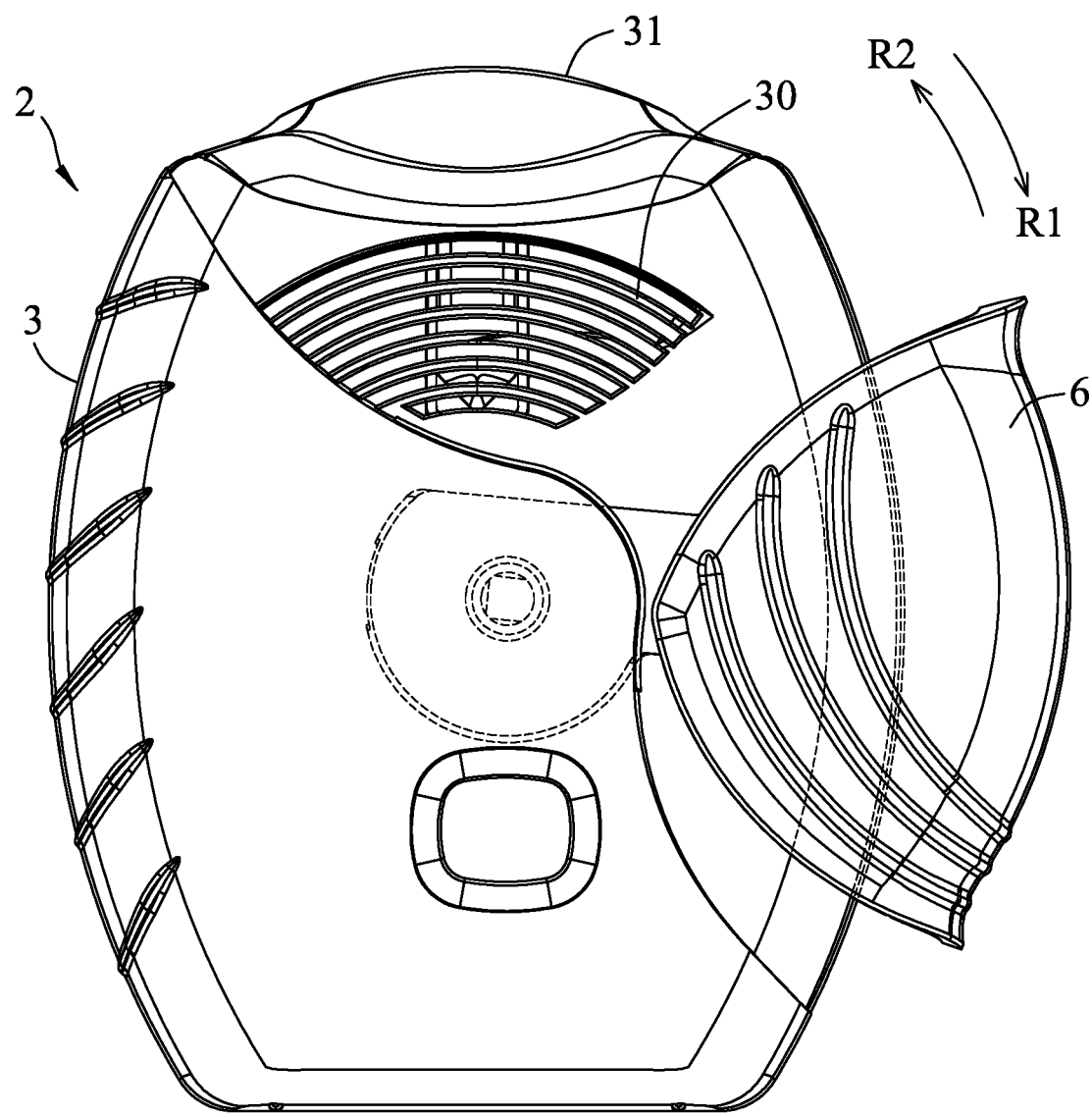
FIG. 1 is a front view illustrating a first embodiment of a medication dispenser according to the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

Figure 2:
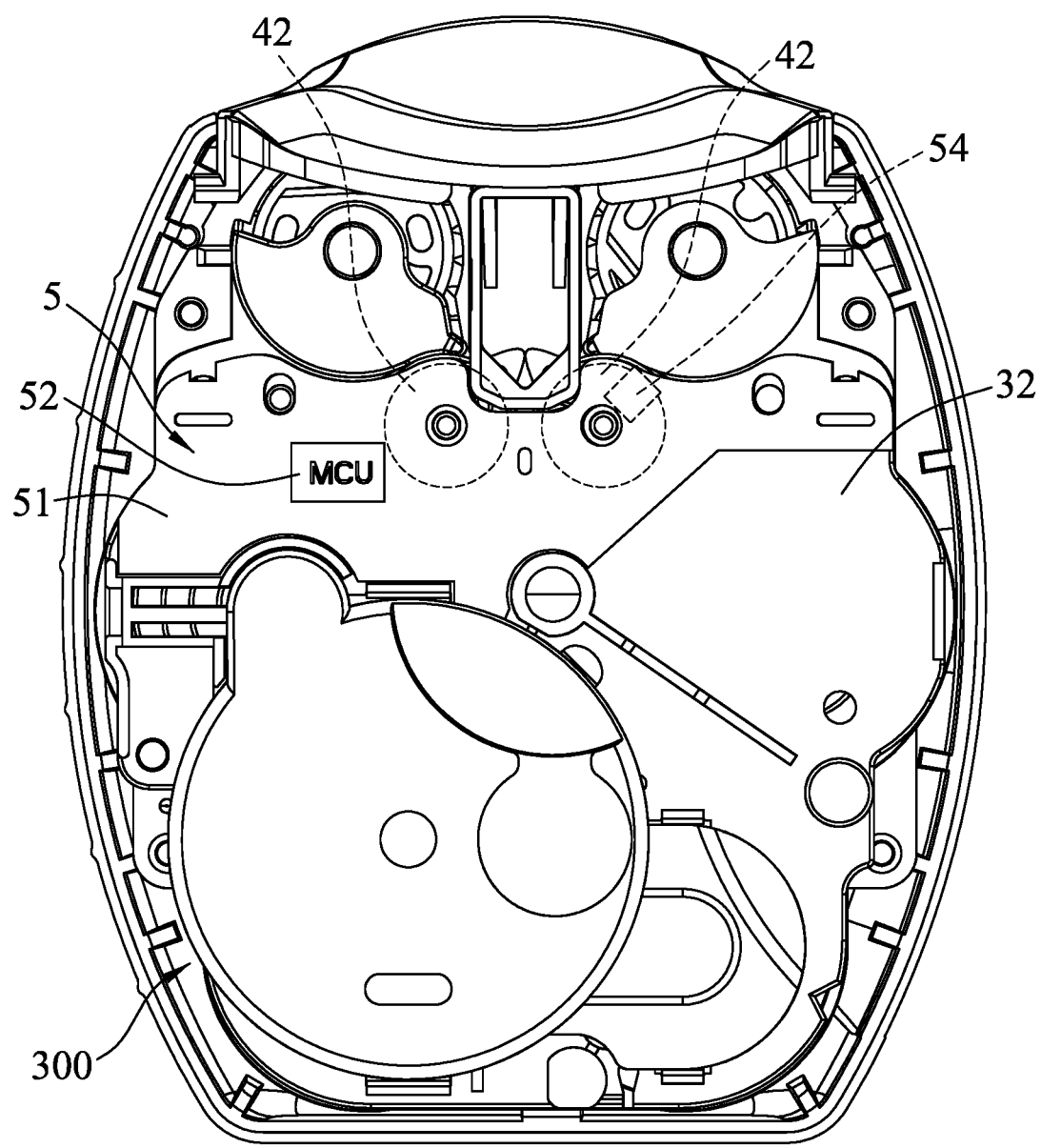
FIG. 2 is a cutaway front view illustrating the first embodiment.
Figure 3:
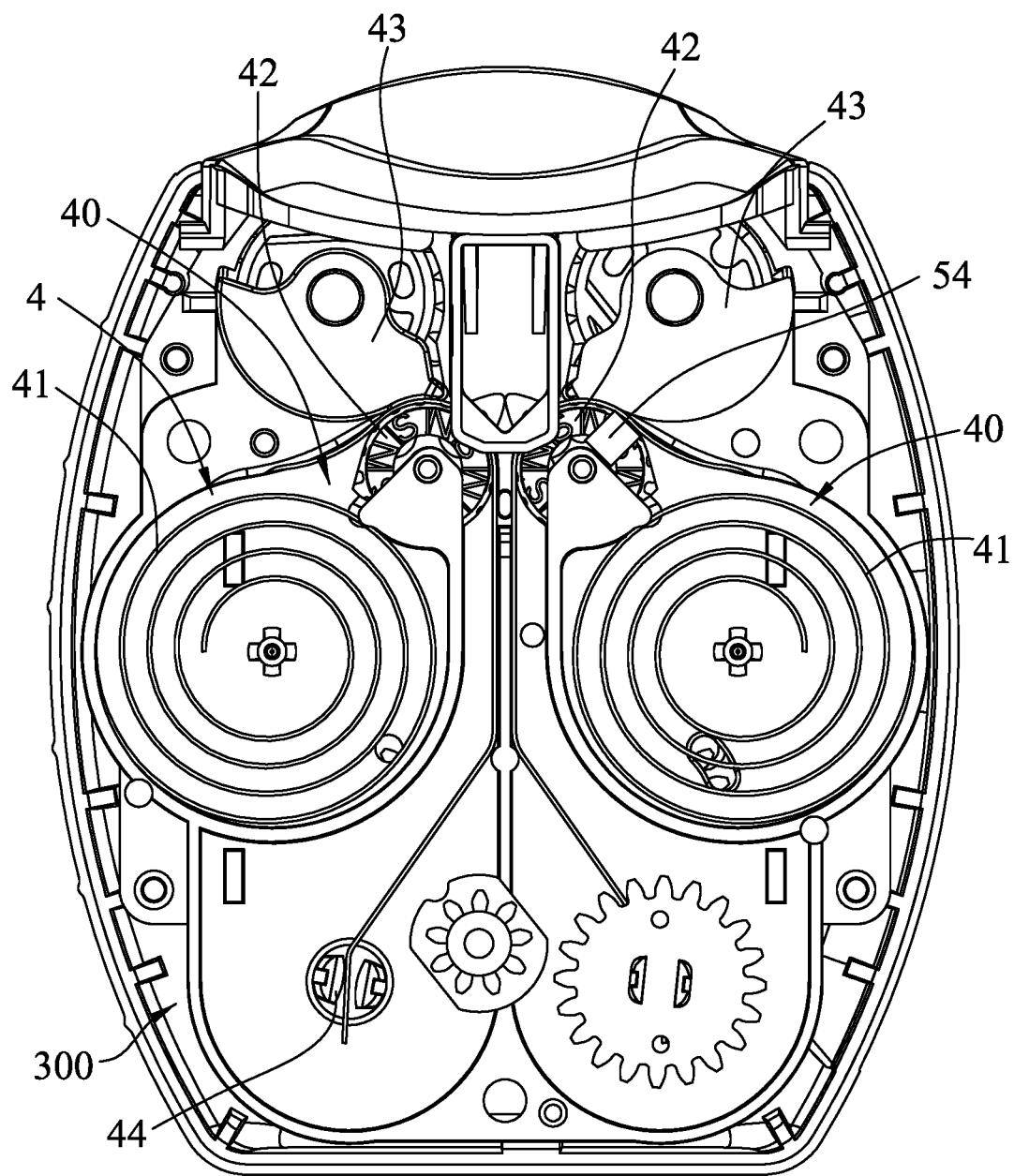
FIG. 3 is another cutaway front view illustrating the first embodiment, omitting a mounting plate.

Referring to FIGS. 1 to 3, the first embodiment of the medication dispenser 2 according to the disclosure includes a casing 3, a dispenser unit 4, a circuitry unit 5 and a cover 6.

The casing 3 defines a retaining space 300 therein that permits the dispenser unit 4 and the circuitry unit 5 to be disposed therein, and includes a mouthpiece 31 at an end thereof for contact with a user's lips. The casing 3 further defines an inlet hole unit 30 that is in fluid communication with the retaining space 300. The cover 6 is rotatably mounted to the casing 3, and is operable to rotate relative to the casing 3 between a close position where the cover 6 covers the mouthpiece 31 and the inlet hole unit 30, and an open position where the cover 6 uncovers the mouthpiece 31 and the inlet hole unit 30 (see FIG. 1).

The medication dispenser 2 further includes a mounting plate 32 disposed in the retaining space 300. The dispenser unit 4 is disposed in the retaining space 300, and is located between the mounting plate 32 and an inner surface of the casing 3. The dispenser unit 4 includes two dispenser assemblies 40. Each of the dispenser assemblies 40 includes a conveying strip 41, a notched wheel 42, an abutment member 43 and a winding wheel 44. The conveying strip 41 extends around the notched wheel 42, and has a plurality of spaced-apart capsules (not shown) each of which contains a dose of powdered medication. An end of the conveying strip 41 is connected to winding wheel 44. The conveying strip 41 extends through a space between the notched wheel 42 and the abutment member 43, and is wound by the winding wheel 44.

Figure 4:
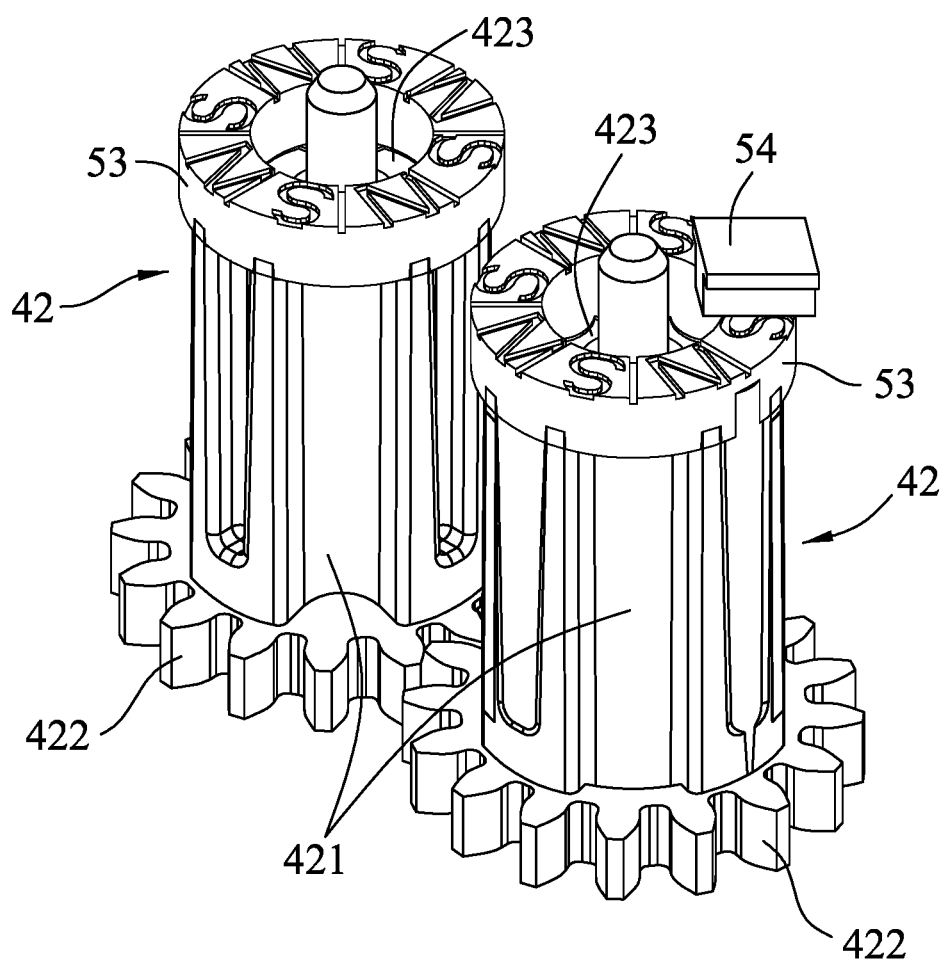
FIG. 4 is a perspective view illustrating two notched wheels of the first embodiment.

Referring further to FIG. 4, which shows the notched wheels 42 of the two dispenser assemblies 40, each of the notched wheels 42 is rotatably mounted to the mounting plate 32, and has a plurality of notches 421 that are formed in an outer surrounding surface thereof. Each of the notches 421 is for receiving one of the capsules of the corresponding conveying strip 41 therein. The notches 421 of one of the notched wheels 42 respectively correspond to the notches 421 of the other one of the notched wheels 42. Each of the notched wheels 42 further has a gear portion 422 at an axial end thereof, and an end surface 423 opposite to the gear portion 422 and proximate to the circuitry unit 5. The gear portions 422 of the notched wheels 42 mesh with each other, such that the notched wheels 42 synchronously rotate, and that one of the notches 421 of one of the notched wheels 42 and the corresponding notch 421 of the other one of the notched wheels 42 are operable to be simultaneously registered with the mouthpiece 31 to permit the medication in the capsules in the two corresponding notches 421 to be simultaneously inhaled.

The circuitry unit 5 includes a circuit board 51, a processor 52 that is mounted to a surface of the circuit board 51 opposite to the notched wheels 42, two annular magnetic members 53 that are respectively mounted to the notched wheels 42, and a Hall sensor 54 that is disposed adjacent to the magnetic members 53.

In one embodiment, the notches 421 of each of the notched wheels 42 are equidistantly and angularly spaced apart from each other, and the number of the notches 421 of each of the notched wheels 42 is even. Each of the magnetic members 53 is a one-piece element, and is co-rotatably mounted to the end surface 423 of the corresponding notched wheel 42. Each of the magnetic members 53 has a plurality of first magnetic poles (N) and second magnetic poles (S) that are alternately arranged in a circumferential direction of the magnetic member 53. The first magnetic poles (N) and the second magnetic poles (S) of each of the magnetic member 53 are alternately arranged on the end surface 423 of the corresponding notched wheels 42, and are equidistantly and angularly arranged in a circumferential direction of the end surface 423 of the corresponding notched wheels 42 (also the circumferential direction of the magnetic member 53). The sum of the number of the first magnetic poles (N) and the number of the second magnetic poles (S) of each of the magnetic members 53 is even. Preferably, the number of the notches 421 of each of the notched wheels 42 is half the sum of the number of the first magnetic poles (N) and the number of the second magnetic poles (S) of each of the magnetic members 53. In one embodiment, the number of the notches 421 of each of the notched wheels 42 is four, the number of the first magnetic poles (N) of each of the magnetic members 53 is four, and the number of the second magnetic poles (S) of each of the magnetic members 53 is four.

The circuit board 51 is disposed in the retaining space 300, and is located at one side of the mounting plate 32 opposite to the dispenser unit 4. In other words, the mounting plate 32 is located between the circuit board 51 and the end surfaces 423 of the notched wheels 42, and the processor 52 is disposed on the surface of the circuit board 51 opposite to the mounting plate 32. The Hall sensor 54 is disposed on a surface of the mounting plate 32 opposite to the circuit board 51, is proximate to the end surfaces 423 of the notched wheels 42, and is electrically connected to the circuit board 51.

In use of the medication dispenser 2, the user may hold the casing 3 and rotate the cover 6 in a first rotational direction (R1) from the close position to the open position. The cover 6 is associated with the notched wheels 42 and the winding wheels 44 of the dispenser assemblies 40 via a one-way transmission mechanism (not shown). The transmission mechanism can be referred to a medical inhaler of GlaxoSmithKline (GSK) named Ellipta Inhaler. The rotation of the cover 6 from the close position to the open position drives each of the notched wheels 42 and the winding wheels 44 of the dispenser assemblies 40 to rotate by a predetermined angle via a one-way transmission mechanism, such that the corresponding notches 421 of the notched wheels 42 are simultaneously registered with the mouthpiece 31 to permit the medication therein to be simultaneously inhaled. After inhalation, the cover 6 may be rotated in a second rotational direction (R2) from the open position to the close position without driving rotation of the notched wheels 42 and the winding wheels 44 of the dispenser assemblies 40.

During the operation of the medication dispenser 2, the Hall sensor 54 is in a first detecting state when it detects a first magnetic pole (N), and is in a second detecting state when it detects a second magnetic pole (S).

It should be noted that, in determining the detection of the first magnetic pole (N) or the second magnetic pole (S), the Hall sensor 54 may not be necessarily located at a position where strength of the magnetic field generated by the first magnetic pole (N) or the second magnetic pole (S) is the strongest. For example, during the rotation of the notched wheels 42 (i.e., the rotation of the magnetic members 53), it is determined that a first magnetic pole (N) or a second magnetic pole (S) is detected by the Hall sensor 54 when the strength of the magnetic field generated by the first magnetic pole (N) or the second magnetic pole (S) exceeds a predetermined threshold. In one embodiment, a first magnetic pole (N) or a second magnetic pole (S) may be determined to be detected by the Hall sensor 54 when the first magnetic pole (N) or the second magnetic pole (S) is registered with the Hall sensor 54.

The Hall sensor 54 generates a signal (e.g., a variation-in-voltage signal) during the switch between the first and second detecting states. In one embodiment, upon the rotation of the cover 6 in the first rotational direction (R1), the Hall sensor 54 generates a signal when it is switched from the first detecting state to the second detecting state and back to the first detecting state or from the second detecting state to the first detecting state and back to the second detecting state. The processor 52 receives the signal generated by the Hall sensor 54 to determine a decrement of the number of the remaining doses of each of the dispenser assemblies 40 by one upon each rotation of the cover 6 in the first rotational direction (R1). It should be noted that, since the notched wheels 42 of the dispenser assemblies 40 synchronously rotate, one of the magnetic members 53 may be omitted. In addition, the magnetic member 53 is not limited to be mounted on the notched wheel 42, and may be co-rotatably mounted to any component of the medication dispenser 2 that is driven to rotate by the rotation of the cover 6 in the first rotational direction (R1) and that is not driven to rotate by the rotation of the cover 6 in the second rotational direction (R2).

In a modification, the Hall sensor 54 may be configured to generate the signal when it is switched from the first detecting state to the second detecting state or from the second detecting state to the first detecting state upon the rotation of the cover 6 in the first rotational direction (R1).

Since the magnetic member 53 is a one-piece element and has alternately arranged first and second magnetic poles (N, S), the magnetic member 53 can be easily mounted to the notched wheel 42, and the notched wheel 42 can be rotated by a relatively small angle for switching the Hall sensor 54 from one of the first and second detecting states to the other. The notched wheel 42 does not need to be formed with a plurality of installation spaces respectively for a plurality of magnets to be mounted thereon with the polarity of the magnets being accurately arranged.

Figure 5:
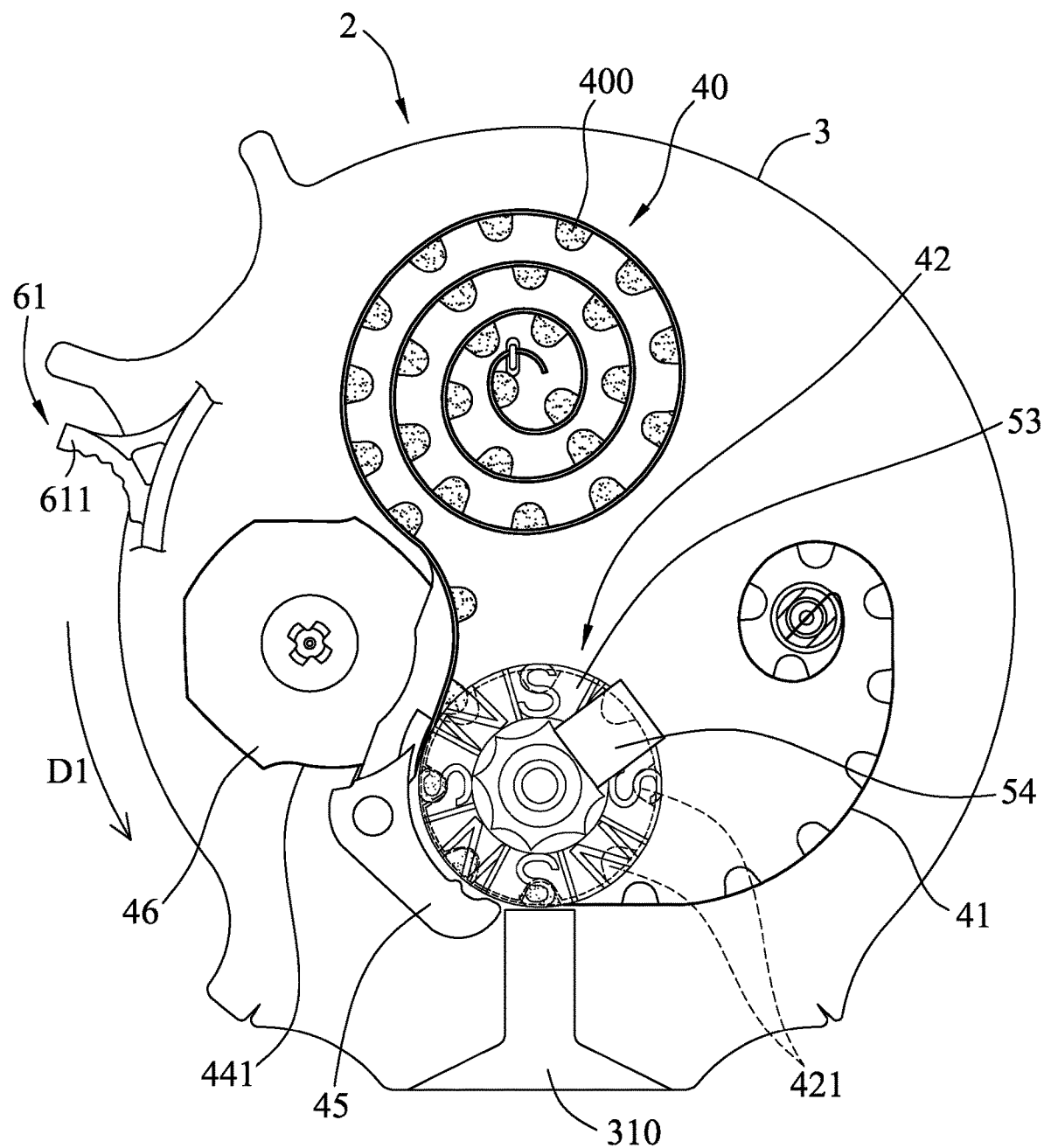
FIG. 5 is a schematic front view illustrating a second embodiment of a medication dispenser according to the disclosure.

Referring to FIG. 5, the second embodiment of the medication dispenser 2 according to the disclosure includes only one dispenser assembly 40. The medication dispenser 2 further includes an operating member 61 that is associated with the dispenser assembly 40 and that has a lever portion 611 projecting out of the casing 3.

The dispenser assembly 40 includes a conveying strip 41, a lid strip 441, a notched wheel 42, a wrapping wheel 46 and a peeler 45. The conveying strip 41 extends around the notched wheel 42, and has a plurality of spaced-apart capsules 400 each of which contains a dose of powdered medication. The lid strip 441 is elongated, and is for sealing the capsules 400 of the conveying strip 41. A portion of the lid strip 441 is separated from the conveying strip 41, and is wound around the wrapping wheel 46. The notched wheel 42 is rotatably mounted to the casing 3, and has a plurality of equidistantly and angularly spaced-apart notches 421 that are formed in an outer surrounding surface thereof. Each of the notches 421 is for receiving one of the capsules 400 therein, so that the conveying strip 41 meshes with the notched wheel 42. The wrapping wheel 46 is rotatably mounted to the casing 3, and wraps the portion of the lid strip 441 that is separated from the conveying strip 41. The annular magnetic member 53 is co-rotatably mounted to the notched wheel 42, and has four first magnetic poles (N) and four second magnetic poles (S) that are alternately arranged in a circumferential direction of the magnetic member 53. In this embodiment, the number of the notches 421 of the notched wheel 42 is eight.

The wrapping wheel 46 and the notched wheel 42 are associated with each other by two gears (not shown) that are respectively and co-rotatably connected to the wrapping wheel 46 and the notched wheel 42 and that mesh with each other. The peeler 45 has a tip portion disposed between the notched wheel 42 and the wrapping wheel 46, and is for separating the lid strip 441 from the conveying strip 41. The operating member 61 is associated with the notched wheel 42 by virtue of a one-way transmission mechanism (not shown). The transmission mechanism can be referred to a medical inhaler of GlaxoSmithKline (GSK) named Diskus Inhaler.

Upon depression of the lever portion 611 of the operating member 61 in a first direction (D1), the notched wheel 42 is rotated to register a notch 421 with the inhalation path 310, and the magnetic member 53 is rotated to switch the Hall sensor 54 from the first detecting state to the second detecting state or from the second detecting state to the first detecting state for counting the remaining dose of medication.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A medication dispenser comprising:
    a casing including a mouthpiece;
    a dispenser unit disposed in said casing and including at least one dispenser assembly, said at least one dispenser assembly including a notched wheel, said notched wheel having an end surface, and a plurality of notches that are formed in an outer surrounding surface thereof for retaining a plurality of doses of medication, said notched wheel being rotatable relative to said casing so as to register said notches with said mouthpiece; and
    a circuitry unit disposed in said casing, and including a circuit board, an annular magnetic member that is co-rotatably mounted to said end surface of said notched wheel, and a Hall sensor that is disposed adjacent to said magnetic member, said magnetic member having a plurality of first and second magnetic poles that are alternately arranged;
    wherein, said Hall sensor is in a first detecting state when it detects one of said first magnetic poles, and is in a second detecting state when it detects one of said second magnetic poles.

2. The medication dispenser as claimed in claim 1, wherein said dispenser unit includes two of said dispenser assemblies, said notches of one of said notched wheels of said dispenser assemblies respectively corresponding to said notches of the other one of said notched wheels, said notched wheels of said dispenser assemblies being configured to synchronously rotate, so that one of said notches of one of said notched wheels and said corresponding notch of the other one of said notched wheels are operable to be simultaneously registered with said mouthpiece, said magnetic member being co-rotatably mounted to said end surface of one of said notched wheels.

3. The medication dispenser as claimed in claim 2, wherein said circuitry unit includes two of said magnetic members that are respectively and co-rotatably mounted to said notched wheels.

4. The medication dispenser as claimed in claim 1, wherein said notches of said notched wheel are equidistantly and angularly spaced apart from each other, the number of said notches of said notched wheels being even, said first magnetic poles and said second magnetic poles of said magnetic member being equidistantly and angularly arranged in a circumferential direction of said magnetic member.

5. The medication dispenser as claimed in claim 4, wherein the number of said notches of said notched wheels is half the sum of the number of said first magnetic poles and the number of said second magnetic poles of said magnetic member.

6. The medication dispenser as claimed in claim 1, wherein said circuitry unit further includes a processor that is mounted to said circuit board, said Hall sensor generating a signal during the switch between the first and second detecting states, said processor receiving the signal generated by said Hall sensor so as to determine a decrement of the number of the doses by one.

7. The medication dispenser as claimed in claim 6, wherein said Hall sensor generates a variation-in-voltage signal when the Hall sensor is switched from the first detecting state to the second detecting state.

8. A medication dispenser comprising
a casing including a mouthpiece;
at least one notched wheel disposed in said casing, and having a plurality of equidistantly and angularly spaced-apart notches that are formed in an outer surrounding surface thereof for retaining a plurality of doses of medication, said notched wheel being rotatable relative to said casing so as to register said notches with said mouthpiece; and
a circuitry unit disposed in said casing, and including a circuit board, an annular magnetic member that is co-rotatably mounted to said end surface of said at least one notched wheel, and a Hall sensor that is disposed adjacent to said magnetic member, said magnetic member having a plurality of first and second magnetic poles that are alternately arranged;
wherein, said Hall sensor is in a first detecting state when it detects one of said first magnetic poles, and is in a second detecting state when it detects one of said second magnetic poles; and
wherein, it is determined that one of said first and second magnetic poles is detected by said Hall sensor when the strength of the magnetic field generated by the one of said first and second magnetic poles exceeds a predetermined threshold.

9. The medication dispenser as claimed in claim 8, comprising two of said notched wheels, said notches of one of said notched wheels respectively corresponding to said notches of the other one of said notched wheels, said notched wheels being configured to synchronously rotate, so that one of said notches of one of said notched wheels and said corresponding notch of the other one of said notched wheels are operable to be simultaneously registered with said mouthpiece, said magnetic member being co-rotatably mounted to said end surface of one of said notched wheels.

10. The medication dispenser as claimed in claim 9, wherein said circuitry unit includes two of said magnetic members that are respectively and co-rotatably mounted to said notched wheels.

11. The medication dispenser as claimed in claim 8, wherein the number of said notches of said notched wheels is even, said first magnetic poles and said second magnetic poles of said magnetic member being equidistantly and angularly arranged in a circumferential direction of said magnetic member.

12. The medication dispenser as claimed in claim 11, wherein the number of said notches of said notched wheels is half the sum of the number of said first magnetic poles and the number of said second magnetic poles of said magnetic member.

13. The medication dispenser as claimed in claim 8, wherein said circuitry unit further includes a processor that is mounted to said circuit board, said Hall sensor generating a signal during the switch between the first and second detecting states, said processor receiving the signal generated by said Hall sensor so as to determine a decrement of the number of the doses by one.

14. The medication dispenser as claimed in claim 13, wherein said Hall sensor generates a variation-in-voltage signal when the Hall sensor is switched from the first detecting state to the second detecting state.

15. A medication dispenser comprising
a casing;
at least one notched wheel disposed in said casing, and having a plurality of equidistantly and angularly spaced-apart notches that are formed in an outer surrounding surface thereof for retaining a plurality of doses of medication, said notched wheel being rotatable relative to said casing so as to permit the doses in said notches to be inhaled; and
a circuitry unit disposed in said casing, and including a magnetic member that is co-rotatably mounted to said at least one notched wheel, and a Hall sensor that is for detecting said magnetic member, said magnetic member having a plurality of first and second magnetic poles that are alternately arranged in a circumferential direction thereof;
wherein, upon rotation of said magnetic member along with said notched wheel, said Hall sensor switches between a first detecting state in which one of said first magnetic poles is detected by said Hall sensor, and a second detecting state in which one of said second magnetic poles is detected by said Hall sensor.

16. The medication dispenser as claimed in claim 15, wherein said magnetic member is configured as a one-piece element.

17. The medication dispenser as claimed in claim 15, comprising two of said notched wheels, said notches of one of said notched wheels respectively corresponding to said notches of the other one of said notched wheels, said notched wheels being configured to synchronously rotate, so that one of said notches of one of said notched wheels and said corresponding notch of the other one of said notched wheels are operable to be simultaneously registered with said mouthpiece, said magnetic member being co-rotatably mounted to said end surface of one of said notched wheels.

18. The medication dispenser as claimed in claim 17, wherein said circuitry unit includes two of said magnetic members that are respectively and co-rotatably mounted to said notched wheels.

19. The medication dispenser as claimed in claim 15, wherein the number of said notches of said notched wheels is even, said first magnetic poles and said second magnetic poles of said magnetic member being equidistantly and angularly arranged in a circumferential direction of said magnetic member.

20. The medication dispenser as claimed in claim 19, wherein the number of said notches of said notched wheels is half the sum of the number of said first magnetic poles and the number of said second magnetic poles of said magnetic member.

\* \* \* \* \*